US00PP23334P3

(12) United States Plant Patent
Korlipara

(10) Patent No.: US PP23,334 P3
(45) Date of Patent: Jan. 15, 2013

(54) *ECHINACEA* PLANT NAMED 'PHOENIX'

(50) Latin Name: ***Echinacea* spp.**
Varietal Denomination: Phoenix

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 105 days.

(21) Appl. No.: 13/068,996

(22) Filed: May 24, 2011

(65) Prior Publication Data
US 2012/0304353 P1 Nov. 29, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Phoenix' characterized by medium, yellow orange ray florets, a medium upright habit, well-branched, strong stems, and good vigor.

1 Drawing Sheet

Botanical denomination: *Echinacea* spp.
Variety designation: 'Phoenix'.

The present invention relates to a new and distinct cultivar of *Echinacea* and given the cultivar name 'Phoenix'. *Echinacea* is in the family Asteraceae. This new cultivar is a fourth generation seedling originating from a planned breeding program using *Echinacea paradoxa* as the seed parent in the original cross and *Echinacea purpurea* 'Ruby Giant' (an unpatented plant) as the pollen parent. The exact parents of this selection are unknown, unnamed, proprietary plants.

Compared to *Echinacea paradoxa,* an unpatented plant and one of the original parents to the breeding line, the new cultivar has a much shorter habit and a flatter inflorescence rather than strongly drooping.

Compared to *Echinacea* 'Tiki Torch' (U.S. Plant Pat. No. 18,839), the new cultivar has lighter orange flowers and a shorter habit.

Compared to *Echinacea* 'Art's Pride' (U.S. Plant Pat. No. 15,090), the new variety has lighter orange ray florets, lighter colored cones, and a shorter habit.

This new *Echinacea* cultivar is uniquely distinguished by:
1. medium, yellow orange ray florets,
2. medium upright habit,
3. well branched, strong stems, and
4. good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences of *Echinacea* 'Phoenix' from a one and a half year old plant grown in the field in full sun in Canby, Oreg.

DETAILED PLANT DESCRIPTION

The following is a detailed description of the new *Echinacea* cultivar based on observations of 9 month-old specimens growing in the 1 gallon pots in full sun outside in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:
- *Type.*—Herbaceous perennial.
- *Hardiness.*—USDA Zones 4 to 9.
- *Size.*—Grows to about 36 cm wide and 61 cm tall to top of inflorescences.
- *Form.*—Basal clump, with 1 to 4 stems from the base.
- *Vigor.*—Excellent.
- *Roots.*—Fibrous, with many downward growing and few laterals, ivory in color, Yellow White 158D, roots develop easily from cuttings from the crown.

Stem (flowering):
- *Type.*—Ascending, with 3 to 11 flowers per stem.
- *Size.*—To 60 cm tall to a terminal inflorescence and 12 mm wide at base.
- *Internode length.*—2 cm to 8.5 cm.
- *Surface texture.*—Strigose.
- *Color.*—Yellow Green 146A.

Leaf (basal):
- *Type.*—Simple.
- *Shape.*—Lanceolate.
- *Arrangement.*—Basal.
- *Blade size.*—Grows to 16 cm long and 4 cm wide.
- *Margins.*—Entire.
- *Apex.*—Acute.
- *Base.*—Attenuate.
- *Surface texture.*—Strigose on both sides.
- *Venation.*—Pinnate.
- *Color.*—Topside Green 137A, bottom side Green 137B.
- *Petiole description.*—Grows to 19 cm long and 3 mm wide, glabrous, Yellow Green 146A.

Leaf (stem):

*Type.*—Simple.

*Shape.*—Lanceolate to ovate.

*Arrangement.*—Alternate.

*Blade size.*—Grows to 13 cm long and 5 cm wide.

*Margins.*—Entire and slightly undulate.

*Apex.*—Acute to acuminate.

*Base.*—Attenuate.

*Surface texture.*—Strigose on both sides.

*Venation.*—Pinnate.

*Color.*—Topside Green 137A bottom side Green 137B.

*Petiole description.*—On lowermost leaves only, clasping, grows to 10 cm long and 3 mm wide above the clasp, scabrous, Yellow Green 146B.

Inflorescence:

*Type.*—Composite on terminal stalked heads.

*Number of flowering stems per plant.*—Between 3 and 11.

*Flowering stem.*—Grows to 60 cm tall from the base of the plant to the terminal inflorescence and can grow to 15 cm long from the top stem leaf to the base of an inflorescence; branched, with 3 to 11 inflorescences per stem; diameter growing to 7 mm wide near the inflorescence; strigose; Yellow Green 146C.

*Size.*—Grows to 8.5 cm wide and 4 cm deep as disc enlarges.

*Form.*—Ray florets held horizontal when young to lightly reflexed when mature, mature disc is conic.

*Immature inflorescence.*—Grows to 3 cm wide and 1.5 cm deep, ray florets held out at a 20 degree angle from the horizontal and rolled up so only the back color shows, Orange 26A, disc color Yellow Green 146A.

*Ray florets.*—Without pistil or stamen, about 25, grow to 4 mm long and 6 mm wide, oblanceolate with the tip two-toothed (each acute), entire margins, base attenuate, glabrous on both sides; topside Yellow Orange 21A; bottom side Yellow Orange 20A.

*Disc.*—Flat becoming conic, becoming 30 mm deep and 39 mm wide with maturity, Green 137A.

*Disc florets.*—About 400 in number, each with 1 pistil and 4 stamen, grow to 8 mm long and 1.5 mm wide, each with one persistent, very stiff linear bract (12 mm long with the tip Greyed Orange N170A to top 2 mm to Green 137B for 3 mm to White NN155A on bottom); corolla 5 mm long and 1.5 mm wide, tubular, 5 lobed, glabrous, Yellow Green 145C to lobe tips Greyed Purple 187A; pistil 9 mm long, ovary 2 mm long, White NN155D, style 4.5 mm long Yellow Green 145D, 2-branched stigma spreading 3 mm wide, Greyed Purple 187A; stamen 5 mm long, filaments 2 mm long and Yellow Green 145D, anthers 3 mm long and Grey Brown 199A, pollen Yellow Orange 23A.

*Phyllaries.*—In 4 leafy series, area grows to 35 mm wide and 10 mm deep, lobes lanceolate in shape, reflexed, grow to 11 mm long and 3.5 mm wide, Yellow Green 147A, margins strigose, tip acute, strigose on both sides.

*Receptacle.*—Grows to 14 mm wide and 12 mm deep, White NN155B.

*Bloom period.*—July through October in Canby, Oreg.

*Fragrance.*—Strong, sweet, floral.

*Lastingness.*—Each inflorescence lasts about two weeks in Canby, Oreg.

Seeds: 3 mm long and 2.5 mm wide, oval, Brown 200C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

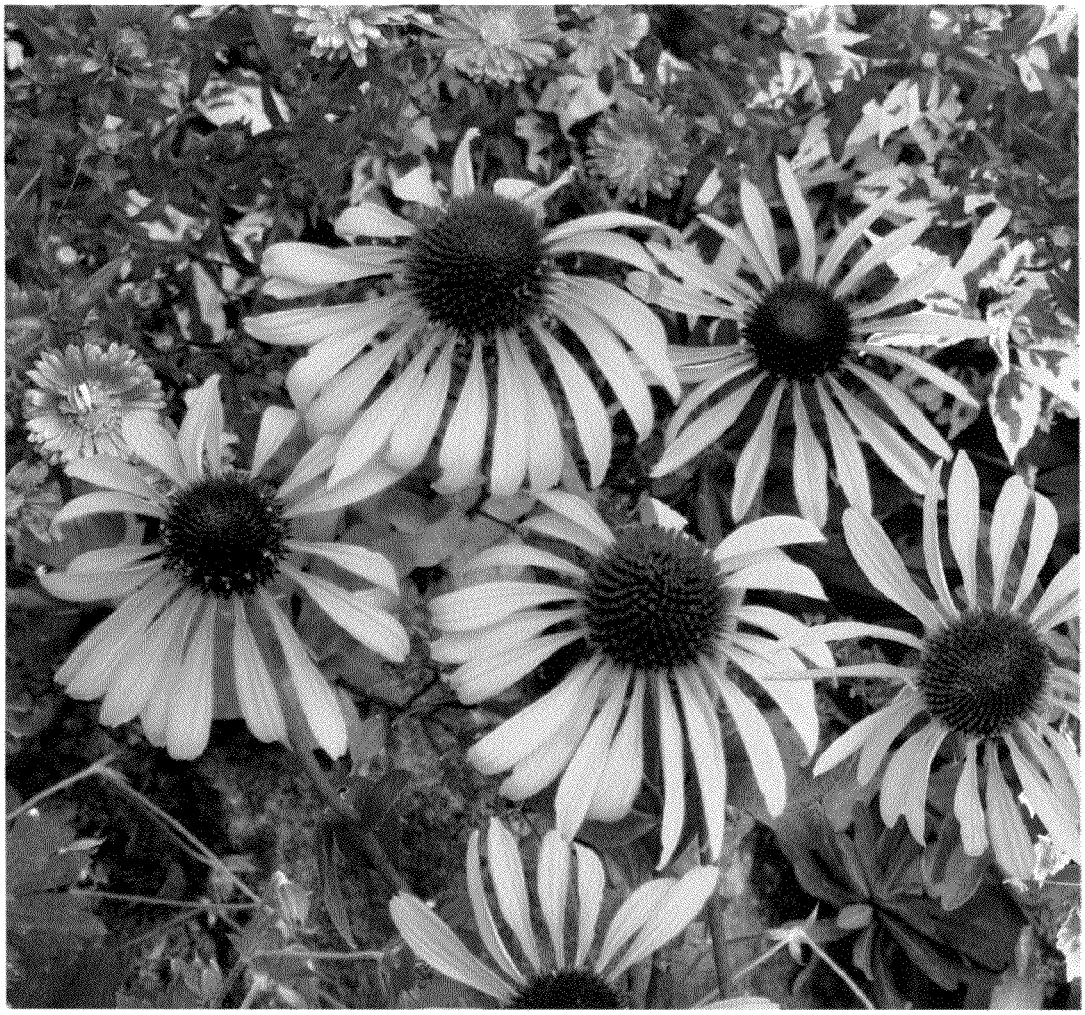

* * * * *